US012708407B2

(12) United States Patent
Biedermann et al.

(10) Patent No.: US 12,708,407 B2
(45) Date of Patent: Aug. 18, 2026

(54) COUPLING DEVICE FOR COUPLING A BONE ANCHOR TO A ROD AND BONE ANCHORING DEVICE WITH SUCH A COUPLING DEVICE

(71) Applicant: BIEDERMANN TECHNOLOGIES GMBH & CO. KG, Donaueschingen (DE)

(72) Inventors: Timo Biedermann, Trossingen (DE); Wilfried Matthis, Weisweil (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 15 days.

(21) Appl. No.: 18/659,918

(22) Filed: May 9, 2024

(65) Prior Publication Data

US 2024/0366268 A1 Nov. 7, 2024

Related U.S. Application Data

(63) Continuation of application No. 17/483,356, filed on Sep. 23, 2021, now Pat. No. 12,004,779, which is a (Continued)

(30) Foreign Application Priority Data

Oct. 21, 2015 (EP) .................................... 15190858

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7035* (2013.01); *A61B 17/8605* (2013.01)

(58) Field of Classification Search
CPC ............ A61B 17/7032; A61B 17/7035; A61B 17/7037; A61B 17/8605
See application file for complete search history.

(56) References Cited

U.S. PATENT DOCUMENTS 5,716,356 A 2/1998 Biedermann et al.
7,604,655 B2 10/2009 Warnick (Continued)

FOREIGN PATENT DOCUMENTS

EP 1 743 584 A1 1/2007
EP 2732782 A1 5/2014

(Continued)

OTHER PUBLICATIONS

Extended European Search Report for Application No. 15190858.9, issued on Apr. 13, 2016, 10 pages.

(Continued)

*Primary Examiner* — Nicholas J Plionis

(74) *Attorney, Agent, or Firm* — Womble Bond Dickinson (US) LLP

(57) ABSTRACT

A coupling device for coupling a bone anchor to a rod includes a receiving part having a longitudinal axis, a channel for receiving a rod, and an accommodation space for holding a head of a bone anchor, a pressure member having a first portion for holding and clamping the head and a deformable portion with a free end, and a locking member. The pressure member is expandable for inserting the head and adjustable to lock the head. When the deformable portion is at a first configuration, the free end of the deformable portion is supported by the receiving part, and at least part of the locking member is movable to exert a force on the deformable portion for adjusting the deformable portion to a second configuration where at least part of the (Continued)

deformable portion is farther away from the longitudinal axis compared to the first configuration.

18 Claims, 8 Drawing Sheets

Related U.S. Application Data continuation of application No. 16/544,252, filed on Aug. 19, 2019, now Pat. No. 11,154,333, which is a continuation of application No. 15/299,165, filed on Oct. 20, 2016, now Pat. No. 10,426,520.

(60) Provisional application No. 62/244,498, filed on Oct. 21, 2015.

(56) References Cited

U.S. PATENT DOCUMENTS

| | | | | |
|---|---|---|---|---|
| 8,075,603 | B2 | 12/2011 | Hammill et al. | |
| 8,088,152 | B2 | 1/2012 | Schumacher | |
| 9,364,266 | B2 | 6/2016 | Biedermann et al. | |
| 9,480,517 | B2 | 11/2016 | Jackson et al. | |
| 9,924,971 | B2 | 3/2018 | Biedermann et al. | |
| 10,058,367 | B2 | 8/2018 | Biedermann et al. | |
| 11,333,192 | B1 | 5/2022 | Lentner et al. | |
| 11,751,916 | B2 | 9/2023 | Jackson et al. | |
| 2005/0154391 | A1 | 7/2005 | Doherty et al. | |
| 2008/0015597 | A1* | 1/2008 | Whipple | A61B 17/7037 606/250 |
| 2008/0269809 | A1 | 10/2008 | Garamszegi | |
| 2008/0294202 | A1* | 11/2008 | Peterson | A61B 17/7037 606/305 |
| 2009/0204155 | A1 | 8/2009 | Aschmann | |
| 2009/0254125 | A1 | 10/2009 | Predick | |
| 2010/0030279 | A1 | 2/2010 | Flynn et al. | |
| 2011/0040336 | A1 | 2/2011 | Hammill, Sr. et al. | |
| 2012/0046699 | A1 | 2/2012 | Jones et al. | |
| 2012/0232598 | A1 | 9/2012 | Hestad et al. | |
| 2012/0253408 | A1 | 10/2012 | Timm | |
| 2013/0096622 | A1 | 4/2013 | Biedermann et al. | |
| 2013/0103093 | A1* | 4/2013 | Biedermann | A61B 17/7035 606/279 |
| 2013/0131734 | A1* | 5/2013 | Longtain | A61B 17/70 606/305 |
| 2013/0150852 | A1 | 6/2013 | Shluzas et al. | |
| 2013/0338721 | A1 | 12/2013 | Biedermann et al. | |
| 2013/0345761 | A1 | 12/2013 | Biedermann et al. | |
| 2014/0142634 | A1 | 5/2014 | Schlaepfer et al. | |
| 2015/0201972 | A1 | 7/2015 | Doubler et al. | |

FOREIGN PATENT DOCUMENTS

| | | | |
|---|---|---|---|
| EP | 2829243 | A1 | 1/2015 |
| EP | 2687172 | B1 | 3/2015 |
| EP | 2851021 | A1 | 3/2015 |
| EP | 2893890 | A1 | 7/2015 |
| WO | WO 2006/116437 | A2 | 11/2006 |

OTHER PUBLICATIONS

Extended European Search Report issued by the EPO for EP 14180588.7 on Feb. 27, 2015, 6 pages.

* cited by examiner

C
81
8
84
74b
75b
74a
7
72a
75a
100
64
69
68
61
6
65
101
58
5a
5
54
51
5b
3
4
1

2
C
8
81
100
84
5
3
1
2

A
A
C

COUPLING DEVICE FOR COUPLING A BONE ANCHOR TO A ROD AND BONE ANCHORING DEVICE WITH SUCH A COUPLING DEVICE

CROSS-REFERENCE TO RELATED APPLICATION(S)

This application is a continuation of U.S. patent application Ser. No. 17/483,356, filed Sep. 21, 2021, which is a continuation of U.S. patent application Ser. No. 16/544,252, filed Aug. 19, 2019, now U.S. Pat. No. 11,154,333, which is a continuation of U.S. patent application Ser. No. 15/299,165, filed Oct. 20, 2016, now U.S. Pat. No. 10,426,520, which claims the benefit of U.S. Provisional Patent Application Ser. No. 62/244,498, filed Oct. 21, 2015, and claims priority from European Patent Application EP 15190858.9, filed on Oct. 21, 2015, the contents of which are hereby incorporated by reference in their entirety.

BACKGROUND

Field

The invention relates to a coupling device for coupling a bone anchor to a rod, and further relates to a bone anchoring device including such a coupling device. The coupling device includes a receiving part with a channel for receiving a rod and an accommodation space for pivotably holding a head of the bone anchor. The head can be locked at an angle by applying pressure onto it via a pressure member. The pressure member has a deformable portion. First, load is applied with a locking member to the pressure member to deform the deformable portion to lock the head. Thereafter, the locking member comes into contact with the rod and locks the rod. The coupling device permits insertion of the bone anchor from a bottom end of the receiving part, thus forming a modular polyaxial bone anchoring device that allows locking of the head and the rod in a sequential manner using a tool with a single drive portion that engages the locking member.

Description of Related Art

US 2013/0345761 A1 describes a polyaxial bone anchoring device including a bone anchoring element with a shank and a head in a receiving part pivotably coupled to the shank and having a channel for receiving a rod. A pressure member is arranged in the receiving part and is configured to exert pressure onto the head to lock the head in the receiving part. The pressure member has a deformable portion. Load applied to the pressure member by a locking member clamps the head, and thereafter the locking member contacts the pressure member such that the deformable portion is deformed and the locking member comes into contact with the rod and clamps the rod.

SUMMARY

While the above device allows the locking of the head in the receiving part first and thereafter the locking of the rod with a single instrument in a sequential manner, the necessary locking force to be applied is high. This results from the fact that the final step of clamping and locking the rod involves the deformation of a deformable portion of the pressure member. The force necessary to effect the deformation may not contribute to and can be lost for the clamping and locking of the rod. To compensate for this, a relatively high force has to be applied for locking the rod.

Embodiments of the invention provide a coupling device for coupling a rod to a bone anchor, and a polyaxial bone anchoring device with such a coupling device that allows for sequential locking of the head and the rod, for example, with an instrument having a single drive portion, where the device has increased versatility with respect to clinical applications.

The coupling device includes a pressure member that exerts pressure onto the head and a deformable portion with a free end that is supported in the receiving part. With a locking member, a force is exerted onto the deformable portion and deforms the deformable portion from a first configuration to a second configuration, wherein the pressure exerted by the pressure member onto the head increases. By means of this, the deformable portion functions similar to a toggle lever that transforms from an angled configuration into a less angled or substantially straight configuration. For locking the rod, the locking member is further advanced and tightened, without further deformation of the deformable portion of the pressure member. Therefore, loss of force due to deformation of the pressure member during locking of the rod is reduced. This permits higher clamping forces acting onto the rod, and in turn increases the safety of the locking.

The coupling device together with a bone anchor forms a polyaxial bone anchoring device of the bottom loading type, wherein the head of the bone anchoring element can be inserted into the receiving part from the bottom side, or from the side opposite to the locking member. Therefore, a modular system can be provided that allows combinations of a variety of bone anchors with the coupling device to form a polyaxial bone anchoring device.

With a polyaxial bone anchoring device according to embodiments of the invention, a sequential locking where first the head is locked and thereafter the rod is fixed by the application of a single instrument with a single drive portion is possible. This facilitates easier handling of the polyaxial bone anchoring device during surgery.

In some embodiments, an optional rod retention member permits holding of an inserted rod, such that the rod cannot move out of the channel even when the rod is not yet locked by the locking member. This can also facilitate easier handling of the polyaxial bone anchoring device during surgery. The polyaxial bone anchoring device including the rod retention member may be of a bottom loading type, or may be of a top loading type, wherein the bone anchoring element is inserted into the receiving part from the top side, or the same side into which the locking member is inserted.

In some embodiments, a shape of the pressure member and optionally of the rod retention member is such that the polyaxial bone anchoring device can be used with rods having different diameters. Thus, the versatility of the polyaxial bone anchoring device can be further increased.

In some embodiments, the deformable portion of the pressure member is elastically deformable and includes a highly elastic material, for example, a material with super-elastic properties, such as a nickel-titanium (NiTi)-alloy, in particular Nitinol, or, for example, Beta-titanium. In these embodiments, due to the high elasticity of the deformable portion, a loss of force during deformation can be further reduced. In addition, due to the elasticity of the deformable portion, size tolerances of the pressure member and of the parts interacting therewith can be more balanced.

BRIEF DESCRIPTION OF THE DRAWINGS

Further features and advantages of the invention will become apparent from the description of embodiments by means of the accompanying drawings. In the drawings.

DETAILED DESCRIPTION

Figures 1, 2:
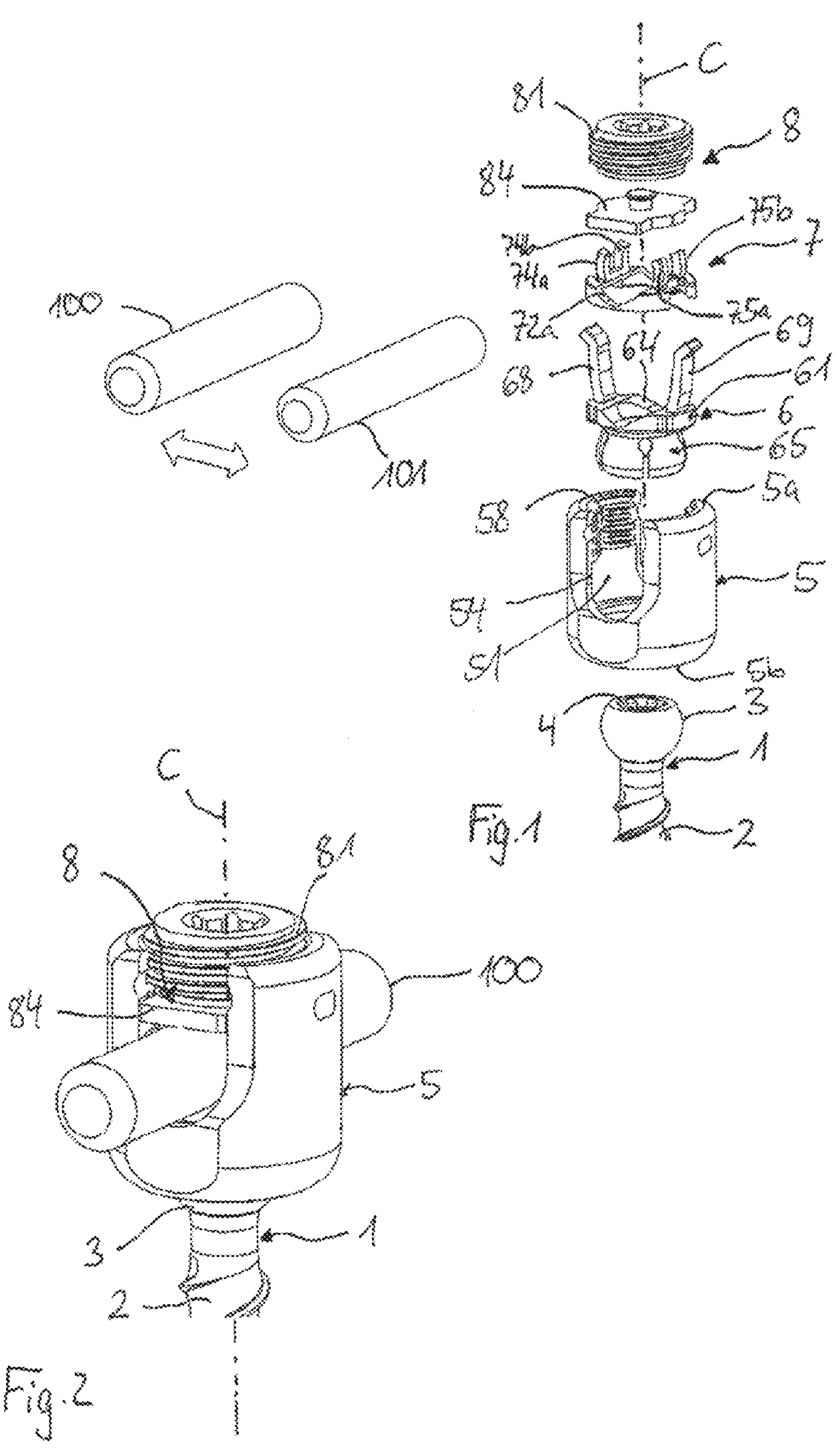
FIG. 1 shows a perspective exploded view of a polyaxial bone anchoring device according to an embodiment of the invention, together with rods having different diameters.
FIG. 2 shows a perspective view of the polyaxial bone anchoring device according to FIG. 1 in an assembled state with an inserted rod.

A polyaxial bone anchoring device according to a first embodiment is shown in FIGS. 1 and 2. The polyaxial bone anchoring device includes an anchoring element 1 having a shank 2 with a threaded portion and a head 3. The head 3 has a spherically-shaped outer surface portion and, on its side opposite to the shank 2, a recess 4 for engagement with a tool. A coupling device including a receiving part 5 is provided for coupling the bone anchoring element 1 to a rod 100 or 101. The polyaxial bone anchoring device in FIGS. 1 and 2 is of the bottom-loading type, or in other words, the bone anchoring element 1 can be inserted into the receiving part 5 from a bottom end of the receiving part 5. In addition, the coupling device includes a pressure member 6 configured to be arranged in the receiving part 5 to exert pressure onto the head 3 of the bone anchoring element 1. To hold an inserted rod temporarily in place, an optional rod retention member 7 can be provided. For locking the head 3 and the rod 100 or the rod 101 relative to the receiving part 5, a locking member 8 is provided that is insertable into the receiving part 5. The coupling device is configured to be used selectively with the rod 100 having a first diameter, or with another rod 101 having a second diameter different from the first diameter, for example a smaller diameter.

Referring further to FIGS. 1 to 6, the receiving part 5 has a first end or top end 5*a* and a second end or bottom end 5*b*, and has a substantially cylindrical construction, with a longitudinal axis C that goes through the top end 5*a* and the bottom end 5*b*. Coaxial with the longitudinal axis C, a coaxial first bore 51 is provided that extends from a distance from the top end 5*a* to a distance from the bottom end 5*b*. A hollow space that is substantially rotationally symmetrical is formed between the bottom end 5*b* and the first bore 51, which serves as an accommodation space 52 for the head 3. The accommodation space 52 has a bottom opening 52*a* at the bottom end 5*b* with an inner diameter that is greater than an outer diameter of the head 3. This permits insertion of the head 3 through the opening 52*a* from the bottom end 5*b*. An inner diameter of the accommodation space 52 at the junction to the first bore 51 is smaller than a diameter of the first bore 51, such that a shoulder 52*b* is formed at the junction. The accommodation space 52 further has a greater diameter approximately midway between the junction to the coaxial bore 51 and the opening 52*a*. A size of the accommodation space 52 is such that the pressure member 6 can be expanded therein when the head 3 is inserted. Adjacent to the opening 52*a*, there is a narrowing portion 52*c* that is configured to engage a narrowing portion of the pressure member 6. The narrowing portion 52*c* may have a tapered shape or a spherical segment shape or any other shape that permits compression of a lower end of the pressure member 6. An edge 52*d* may be formed at a distance from the bottom end 5*b* that protrudes into the accommodation space 52 and contributes to the compression of the pressure member 6.

Between the top end 5*a* and the first bore 51, a coaxial second bore 53 is provided that has a smaller inner diameter than the first bore 51. The receiving part 5 further comprises a U-shaped recess 54 starting at the top end 5*a* and extending in the direction of the bottom end 5*b*. By means of the U-shaped recess 54, two free legs 55, 56 are formed that define a channel for receiving the rod 100 or the rod 101. Adjacent to the top end 5*a* an internal thread 57 is provided at the inner surface of the legs 55, 56 in the region of the second bore 53. In the embodiment shown, the internal thread 57 is a flat thread having substantially horizontal upper and lower thread flanks. However, any other thread form can be used for the internal thread 57. As depicted more in detail in FIGS. 3, 4 and 6, recesses 53*a*, 53*b* are respectively provided at the legs 55, 56 below a lower side of an uppermost thread turn of the internal thread 57 to accommodate a portion of the pressure member 6 therein, so that a first abutment or stop 57*a* for a portion of the pressure member 6 is provided by the lower side of the uppermost thread turn of the thread 57.

Figures 3, 4, 5, 6:
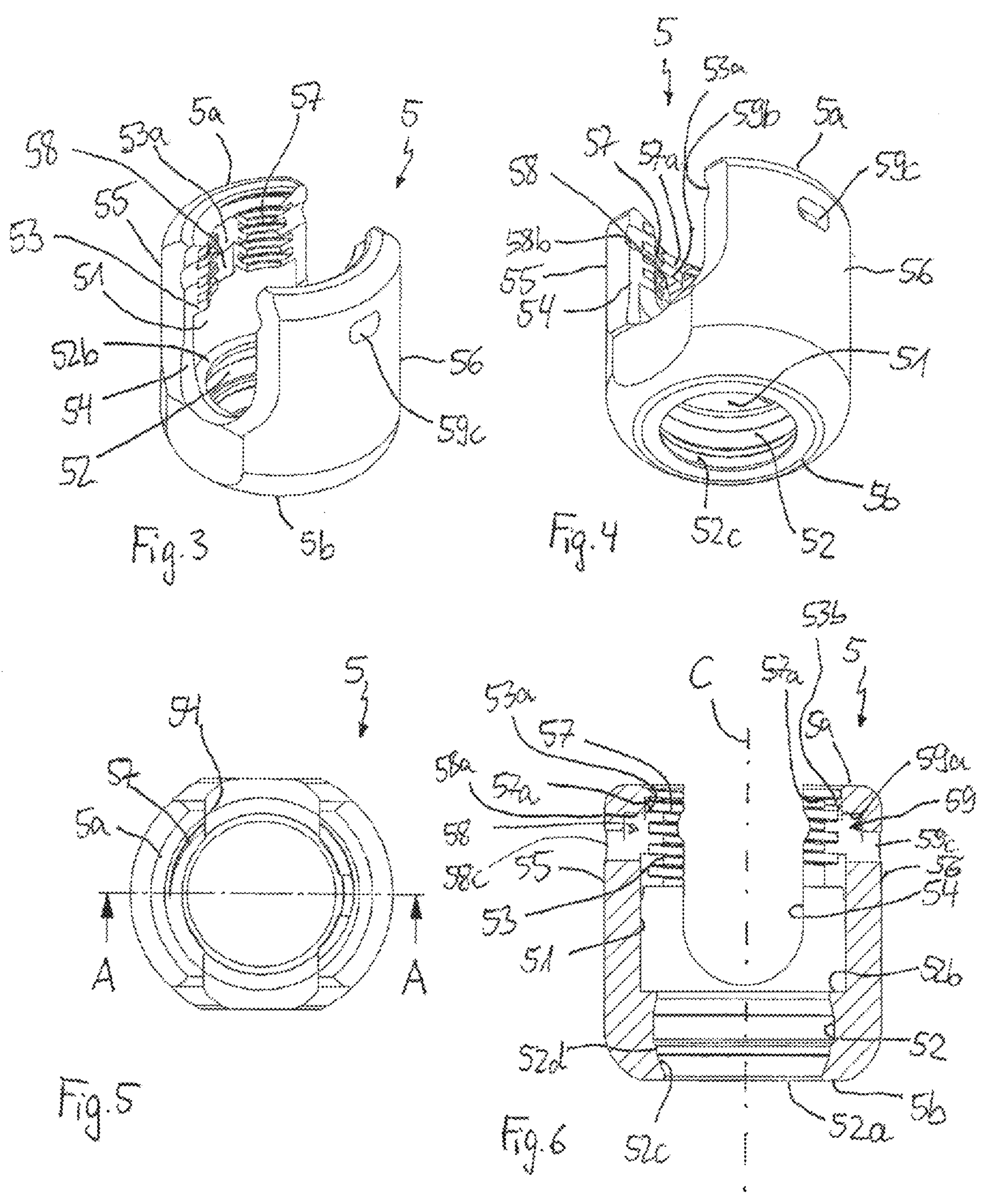
FIG. 3 shows a perspective view from a top of a receiving part of the polyaxial bone anchoring device according to FIGS. 1 and 2.
FIG. 4 shows a perspective view from a bottom of the receiving part of FIG. 3.
FIG. 5 shows a top view of the receiving part of FIGS. 3 and 4.
FIG. 6 shows a cross-sectional view of the receiving part of FIGS. 3 to 5, the cross-section taken along line A-A in FIG. 5.
Figures 7, 8, 9, 10:
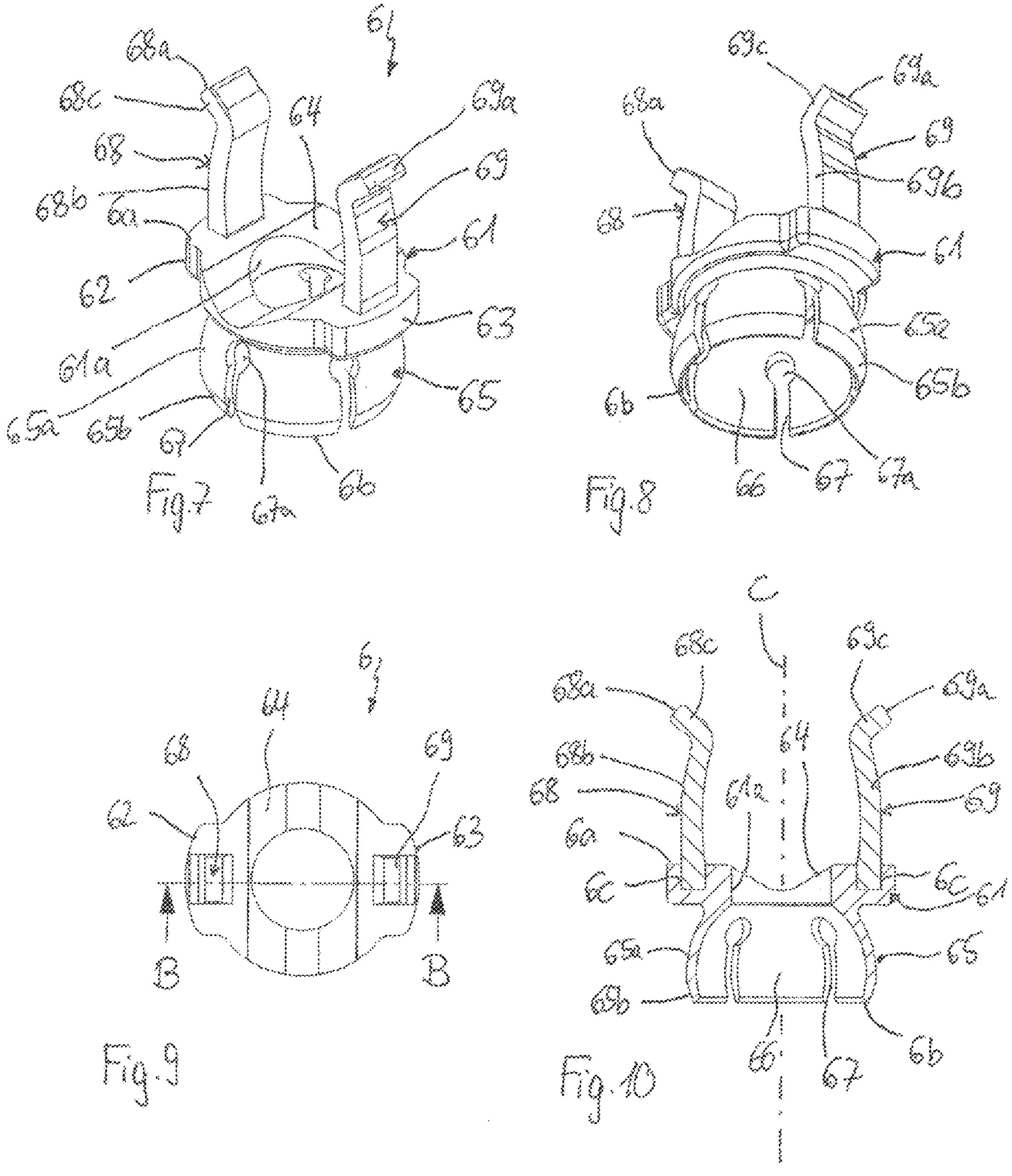
FIG. 7 shows a perspective view from a top of a pressure member of the polyaxial bone anchoring device of FIGS. 1 and 2.
FIG. 8 shows a perspective view from a bottom of the pressure member of FIG. 7.
FIG. 9 shows a top view of the pressure member of FIGS. 7 and 8.
FIG. 10 shows a cross-sectional view of the pressure member of FIGS. 7 to 9, the cross-section taken along line B-B in FIG. 9.

As depicted in particular in FIGS. 3 and 6, two recesses 58, 59 are respectively formed at an inner wall of the legs 55, 56 in the region of the coaxial second bore 53, and are configured to accommodate a portion of the pressure member 6 therein. The recesses 58, 59 are respectively located at substantially the center of each leg 55, 56 in a circumferential direction, at a lower portion of the thread 57, and open into the first bore 51 as well as into the recesses 53*a*, 53*b* described above. An upper wall or a corner of each of the recesses 58, 59 forms a support 58*a*, 59*a* for the pressure member 6. Simultaneously, this support 58*a*, 59*a* forms a second stop for preventing the pressure member 6 from moving towards the top end 5*a* when the pressure member 6 is in a pre-locking position. Moreover, in order to facilitate the placement of the pressure member 6, a shallow groove 58*b*, 59*b* is formed on the inner wall of each leg 55, 56, respectively, at the region of the U-shaped recess 54 at either side of the channel and at approximately the height of the supports 58*a*, 59*a*.

Moreover, through-holes 58*c*, 59*c* may be provided in the receiving part 5 that extend in a transverse direction through walls of the receiving part 5 and into the recesses 58, 59, respectively. The through-holes 58*c*, 59*c* may facilitate application of an instrument for acting onto a portion of the pressure member 6.

Referring now to FIGS. 1 and 7 to 10, the pressure member 6 has a substantially cylinder segment-shaped first portion 61 with two side flanges 62, 63 provided on opposite sides of the first portion 61 and also having cylindrical outer surface portions. At a top surface 6*a* of the pressure member 6 between the flanges 62, 63, a rod supporting surface 64 is provided in the form of a substantially V-shaped recess with a longitudinal axis perpendicular to a central axis C that aligns with the central axis C of the receiving part 5 when a pressure member 6 is mounted to the receiving part 5. The rod supporting surface 64 is configured to support rods 100, 101 of different diameters. In addition, a diameter of an inserted rod is between a maximum and a minimum diameter, the rod can always be safely supported by the rod supporting surface, for example, along two longitudinal contact lines. The pressure member 6 further includes on a side opposite to the top surface 6*a* a second portion 65 that is recessed with respect to the first portion 61. The second portion 65 has a hollow interior 66, which is substantially spherically shaped to clamp the spherical head 3 therein and is open at a second end 6*b* of the pressure member 6. An outer wall of the second portion 65 includes a first portion 65*a* that is substantially spherical and a narrowing portion 65*b* that narrows towards the second end 6*b*. The narrowing portion 65*b* is configured to cooperate with the narrowing portion 52*c* of the receiving part 5. The narrowing portion 65*b* may be tapered or spherical or shaped in another manner, and may not necessarily correspond to the shape of the narrowing portion 52*c* of the receiving part 5, as long as the narrowing portion 65*b* can be compressed by the narrowing portion 52*c* of the receiving part 5. The second portion 65 of the pressure member 6 further has a plurality of slits 67 extending from the free end 6*b* through at least part of the second portion 65. A number and dimensions of the slits 67 are such that a wall of the second portion 65 is flexible enough to snap onto the head 3 when the head 3 is being inserted. The slits 67 may have enlarged portions 67*a* at their closed ends. A coaxial bore 61*a* extends through the first portion 61 into the hollow interior 66 for providing access to the screw head 3 by an instrument.

As shown in the figures, two upstanding arms 68, 69 protrude from the upper surface 6*a* of the first portion 61 of the pressure member 6. The arms 68, 69 are respectively positioned substantially at the middle of the upper surface 6*a* of the flanges 62, 63, and each arm 68, 69 has a substantially rectangular cross-section. In the embodiment shown, a long side of the rectangle is substantially parallel to a longitudinal axis of the rod supporting surface 64 and is smaller than a width of the flanges 68, 69 in this same direction. A width of each of the arms 68, 69 in a direction perpendicular to the longitudinal axis of the rod supporting surface 64 is also smaller than the width of the flanges 68, 69 in the same direction, so that the arms 68, 69 are spaced apart from the edges of the flanges 62, 63. In addition, a thickness of the arms 68, 69 may decrease in an upward direction, away from the first portion 61, to facilitate flexion.

As further shown in particular in FIGS. 7 to 10, each arm 68, 69 has a free end 68*a*, 69*a*. Adjacent to the upper surface 6*a*, each of the arms 68, 69 has a substantially vertically extending long portion 68*b*, 69*b*. From the end of the long portions 68*b*, 69*b*, short portions 68*c*, 69*c* extend radially outward and away from the long portions 68*b*, 69*b* at an angle of substantially 90° or greater. The long portions 68*b*, 69*b* may be twice as long as the short portions 68*c*, 69*c*, or longer. A length of the arms 68, 69 is such that the long portions 68*b*, 69*b* extend above an upper surface of a rod that is placed onto the rod support surface 64. The long portions 68*b*, 69*b* may be slightly curved in an outward direction, i.e. away from the central axis C. As can be seen in particular in FIG. 10, the arms 68, 69 may be separate parts that may be mounted to the first portion 61 of the pressure member 6. More specifically, the arms 68, 69 may be inserted in corresponding recesses 6*c* in the upper surface 6*a* of the first portion 61 of the pressure member 6.

The arms 68, 69 may be elastically deformable in such a manner that they can be deflected outward by an applied load, and can return to their original shape and position once the load is relieved or removed. In particular, in a first configuration, the arms 68, 69 are in their resting position that is defined by the bent shape wherein the short portions 68*c*, 69*c* form an obtuse angle with the long portions 68*b*, 69*b*. In a second configuration, the arms 68, 69 are deformed such that the angle between the short portions 68*c*, 69*c* and the long portions 68*b*, 69*b* is increased, and the long portions 68*b*, 69*b* may be deflected outward. In the second configuration, a load can be transferred through the arms 68, 69 onto the head 3. In other words, the pressure member 6 can behave similar to a toggle lever formed by the arms 68, 69 that act between the receiving part 5 and the head 3.

Figures 18A, 18B, 18C, 18D:
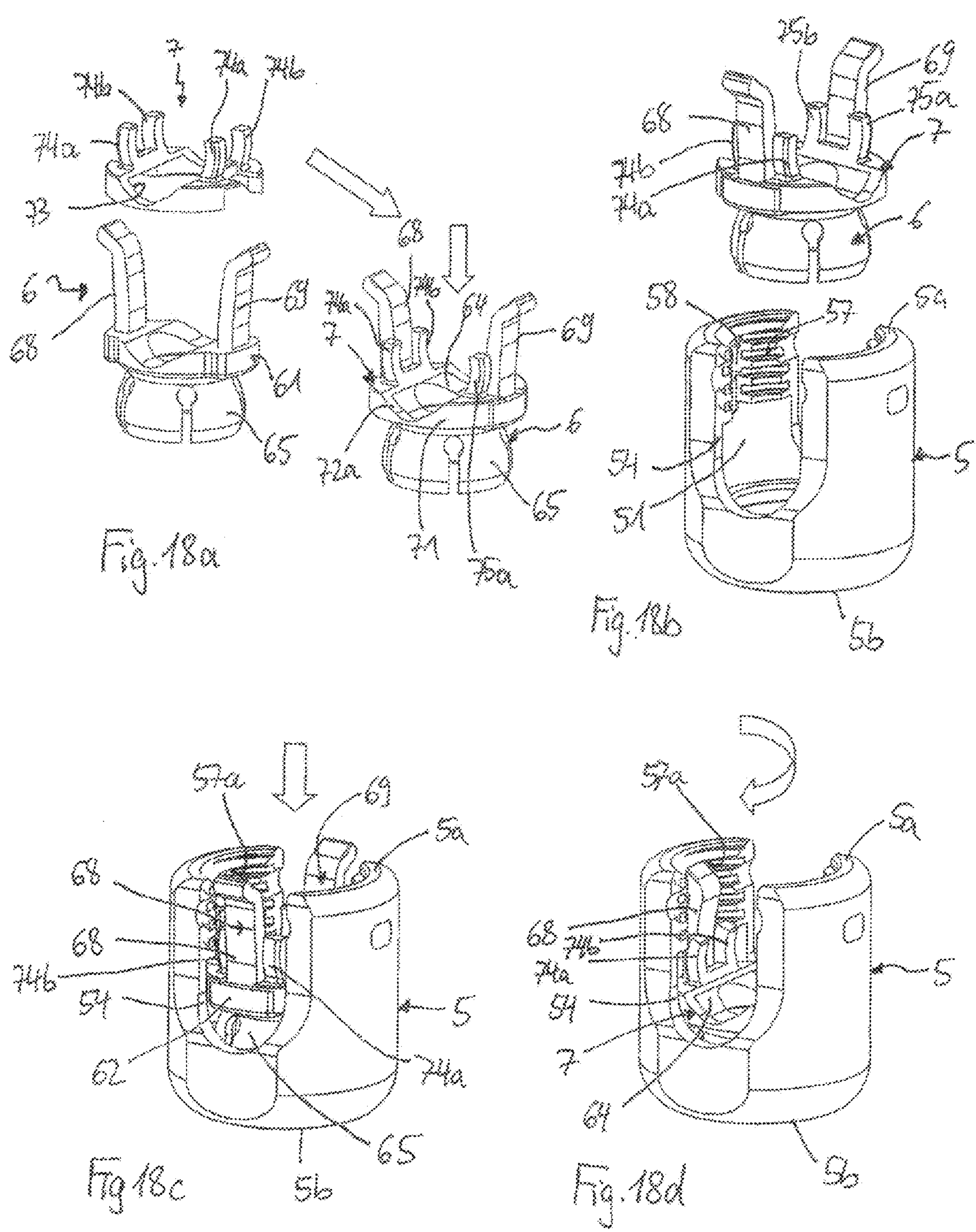
FIGS. 18*a* to 18*d* show perspective views of steps of assembling a coupling device of the polyaxial bone anchoring device of FIGS. 1 and 2.

Referring to FIGS. 1 and 11 to 14, in this embodiment, the rod retention member 7 is a separate part that is configured to be connected to the pressure member 6. The rod retention member 7 has a generally cylindrical base portion 71 with a top surface 7*a* and an opposite bottom surface 7*b*. At the top surface 7*a*, a recess configured to support the rod is formed with a substantially cylindrical first section 72*a* having a first radius and a substantially cylindrical second section 72*b* having a second radius smaller than the first radius. Further, a cut-out 73 is provided that matches the shape of the rod supporting surface 64 of the pressure member 6 such that, as depicted in FIG. 18*a*, when the rod retention member 7 is mounted to the pressure member 6, the rod supporting surface 64 of the pressure member can extend through the cut-out 73. From the top surface 7*a*, a pair of arms 74*a*, 74*b*, 75*a*, 75*b* extend upward on either side of the rod supporting surface 72*a*, 72*b* when seen along a rod axis. An inner surface of the arms 74*a*, 74*b*, 75*a*, 75*b* is substantially cylindrical, with a radius that may be adapted to a radius of a particular rod. A distance between the inner surface of opposite arms 74*a*, 75*a*, or 74*b*, 75*b* is configured such that the inserted rod can be held tightly therebetween. A height of the arms 74*a*, 74*b*, 75*a*, 75*b* in the axial direction is such that when one of the insertable rods is inserted between the arms 74*a*, 74*b*, 75*a*, 75*b* and rests on the rod supporting surface 64, the arms 74*a*, 74*b*, 75*a*, 75*b* are configured to clamp the inserted rod between them.

The arms 74*a*, 74*b*, 75*a*, 75*b* may each also be curved in an outward direction and may have substantially a square-shaped cross-section. As shown in the embodiment, the arms are shorter in length compared to the arms 68, 69 of the pressure member 6. A distance between each pair of arms 74*a*, 74*b* or 75*a*, 75*b*, respectively, is such that the arms 68, 69 of the pressure member 6 can be placed or positioned at least partially between the corresponding arms 74*a*, 74*b*, 75*a*, 75*b* of the rod retention member 7. At the bottom surface 7*b*, a substantially cylindrical recess 76 is provided, the depth of which is such that the rod retention member 7 can be placed onto the first portion 61 of the pressure member 6 in such a manner that the bottom surface 7*b* of the rod retention member is substantially flush with a bottom side of the first portion 61 of the pressure member 6, as can be seen, for example, in FIG. 18*b*. On an outside of the arms 74*a*, 74*b*, 75*a*, 75*b*, a first recess 77*a*, 78*a* is respectively formed in the top surface 7*a* for permitting the arms 68, 69 of the pressure member 6 to extend therethrough. A further recess 77*b*, 78*b* is provided in the bottom surface 7*b* that is in communication with the first recess 77*a*, 78*a* and the recess 76 and permits the flanges 62, 63 of the pressure member 6 to extend therethrough, as shown in FIGS. 18*a* and 18*b*.

Figures 11, 12, 13, 14, 15, 16:
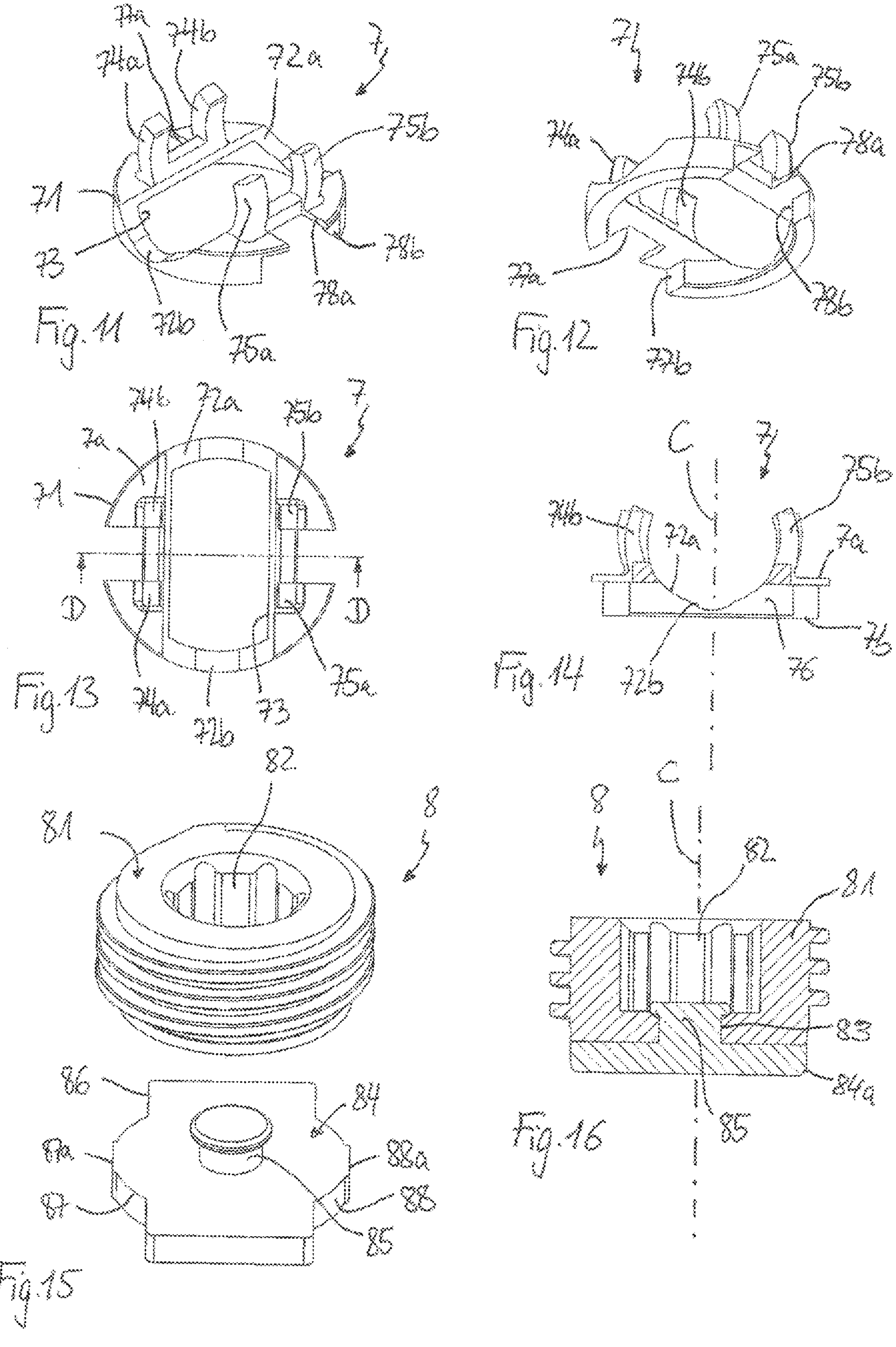
FIG. 11 shows a perspective view from a top of a rod retention member of the polyaxial bone anchoring device according to FIGS. 1 and 2.
FIG. 12 shows a perspective view from a bottom of the rod retention member of FIG. 11.
FIG. 13 shows a top view of the rod retention member of FIGS. 11 and 12.
FIG. 14 shows a cross-sectional view of the rod retention member of FIGS. 11 to 13, the cross-section taken along line D-D in FIG. 13.
FIG. 15 shows a perspective exploded view of a locking member of the polyaxial bone anchoring device of FIGS. 1 and 2.
FIG. 16 shows a cross-sectional view of the locking member of FIG. 15 in an assembled state, the cross-section taken in a plane including a central axis C of the locking member.

The arms 74*a*, 74*b*, 75*a*, 75*b* are resilient in a manner such that they can be deflected outward and snap back to their resting position, for example, as illustrated by the full lines and the dashed lines in FIG. 14.

Referring now in particular to FIGS. 1 and 2 as well as FIGS. 15 and 16, the locking member 8 can be a two-part locking member that includes a set screw 81 and a washer 84 rotatably connected to the set screw 81. The set screw 81 is configured to engage the internal thread 57 of the legs 55, 56 and has an engagement portion 82 for a driver on its upper side. A through-hole 83 may be provided on the lower side of the set screw 81. The washer 84 may be connected to the set screw 81 with a central coaxial pin 85 that extends through the through-hole 83, and for example, that can be deformed on the other side of the through-hole 83 to provide a rivet-like connection. A lower edge 84*a* of the washer 84 may be rounded. This ensures a smooth sliding contact between the locking member 8 and the pressure member 6. The washer 84 has a substantially rectangular main portion 86 and two opposite cylinder-segment shaped flanges 87, 88 that extend from the main portion 86 on opposite sides. The flanges 87, 88 each has a substantially vertically extending substantially flat outermost surface portion 87*a*, 88*a* with a width in a direction perpendicular to the central axis that is substantially the same or greater than the width of the arms 68, 69 of the pressure member 6. By means of this, the washer 84 can smoothly slide along the inner surface of the arms 68, 69 of the pressure member 6 when the locking member 8 is advanced in the receiving part 5. The substantially flat vertical surface portions 87*a*, 88*a* allow for a better transfer of the pressure force applied by the washer 84 onto the arms 68, 69. The rectangular main portion 86 prevents the washer 84 from rotating when the set screw 81 is screwed into the receiving part 5. Therefore, occurrences of transverse forces acting onto the arms 68, 69 is avoided.

The receiving part 5, the pressure member 6, the rod retention member 7, the bone anchoring element 1, and the locking member 8 can each be made of any body-compatible material, such as a body-compatible metal or metal alloy, for example, stainless steel, titanium, or magnesium, or of a body-compatible plastic, such as polyether ether ketone (PEEK) or poly-L-lactide acid (PLLA). The respective parts can all be made of the same or of different materials. In particular, the entire pressure member 6 may be made of a material exhibiting high elasticity, such as a nickel-titanium alloy exhibiting super-elastic properties, for example Nitinol, or Beta-titanium. Alternatively, only the arms 68, 69 of the pressure member 6 can be made of such a highly elastic material. The rod retention member 7 can be made of a body-compatible plastic material as mentioned above, for example, PEEK, while the remaining parts can be made of a metal or metal alloy as mentioned above.

Referring to FIGS. 18*a* to 18*d*, the coupling device may be pre-assembled as follows. In a first step, as depicted in FIG. 18*a*, the rod retention member 7 is mounted onto the pressure member 6 such that the rod supporting surface 64 extends through the cut-out 73 in a manner such that an inserted rod rests only on the rod supporting surface 64 of the pressure member 6 and not on the surfaces 72*a*, 72*b* of the rod retention member 7. The arms 74*a*, 74*b* extend to the left and to the right of the arm 68 of the pressure member 6. The arms 75*a*, 75*b* extend to the left and to the right of the arm 69 of the pressure member 6. The assembly of the pressure member 6 and the rod retention member 7 is then inserted into the receiving part 5, as illustrated in FIGS. 18*b* and 18*c*. To accomplish this, the assembly is orientated relative to the receiving part 5 in a manner such that the arms 68, 69 of the pressure member 6 are aligned with the U-shaped recess 54 of the receiving part 5. The assembly is moved downward until the free ends 68*a*, 69*a* of the arms 68, 69 of the pressure member 6 are beneath the first stop 53*a* on the upper portion of the legs 55, 56. Thereafter, the assembly is rotated, as depicted in FIG. 18*d*, until the arms 68, 69 of the pressure member can extend into the second bore 53 of the receiving part 5.

Figures 19A, 19B, 19C, 19D:
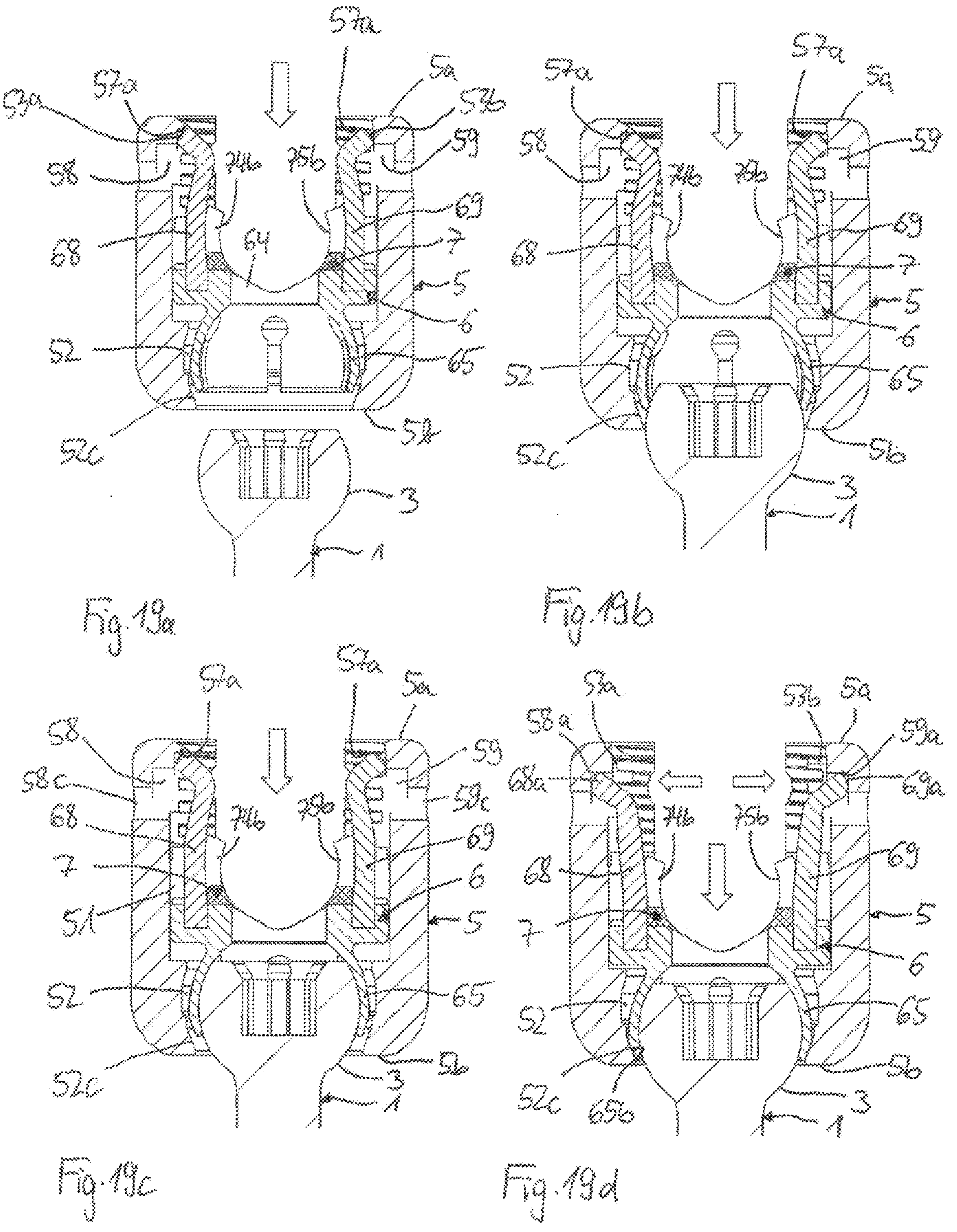
FIGS. 19*a* to 19*d* show cross-sectional views of steps of inserting a head of the bone anchoring element into the receiving part of the coupling device when assembling the polyaxial bone anchoring device.

Steps of assembling the bone anchoring device are now explained with reference to FIGS. 19*a* to 19*d*. In FIG. 19*a*, the pressure member 6 is at an insertion position in which the head 3 of the bone anchoring element can be inserted into the hollow interior 66 of the cap-like second portion 65. The free ends 68*a*, 69*a* of the arms 68, 69 abut against the first stop 53*a* provided in the receiving part 5. In this position, the arms 68, 69 are slightly compressed inwards at their junction between the long portions 68*b*, 69*b* and the short portions 68*c*, 69*c*. The pressure member 6 can not be pushed further upward during insertion of the head 3. The arms 74*a*, 74*b*, 75*a*, 75*b* of the rod retention member 7 extend slightly into the rod receiving channel of the receiving part 5 due to their curved shape. The cap-like second portion 65 of the pressure member 6 is arranged in the accommodation space 52.

As shown in FIG. 19*b*, the head 3 of the bone anchoring element 1 is then inserted through the open end 6*b* into the hollow interior 66 of the pressure member 6. Due to the flexibility of the wall of the cap-like second portion 65 provided by the slits 67, the cap-like second portion 65 expands in the accommodation space 52 and snaps onto the head 3, as shown in FIG. 19*c*. In the insertion position, the head 3 is pivotable in the receiving part 5, and is also removable if the pressure member 6 remains in this position.

As illustrated in FIG. 19*d*, a downward movement of the pressure member 6 with the rod retention member 7 allows the arms 68, 69 to spread once they engage the recesses 58, 59. The free ends 68*a*, 69*a* of the arms 68, 69 abut against the second stop 58*a*, 59*a*. By the downward movement, the pressure member 6 with the inserted head 3 passes the edge 52*d*, and the narrowing portion 52*c* of the receiving part 5 and the narrowing portion 65*b* of the pressure member 6 engage with one another. By means of this, head 3 is held in the receiving part 5. This position of the pressure member 6 as depicted in FIG. 19*d* is a pre-locking position, where the head 3 is still pivotable but cannot be removed through the lower opening 52*a* of the receiving part 5. The pre-locking position is secured by the second stop 58*a*, 59*a*.

It shall be understood that, in some embodiments, the engagement of the head 3 of the anchoring element 1 with the inner wall of the cap-like second portion 65 of the pressure member 6 can be a frictional engagement, so that in the insertion position or even more in the pre-locking position, the head 3 is pivotable when the friction force is overcome. This allows maintaining of the receiving part 5 relative to the bone anchoring element 1 in an adjustable angular position.

In use, the bone anchoring device can be, for example, pre-assembled in such a way that a suitable bone anchoring element 1 is selected and inserted into the receiving part 5 with inserted pressure member 6 and optionally inserted rod retention member 7. The bone anchoring device can be brought into the pre-locking position by slightly pushing down the pressure member 6 relative to the receiving part 5. Then, the bone anchoring element 1 can be implanted into a bone. In an alternative manner, the bone anchoring element 1 is first implanted into the bone, and thereafter the coupling device is mounted onto the head 3 of the bone anchoring element 1.

Figures 20A, 20B, 20C, 20D:
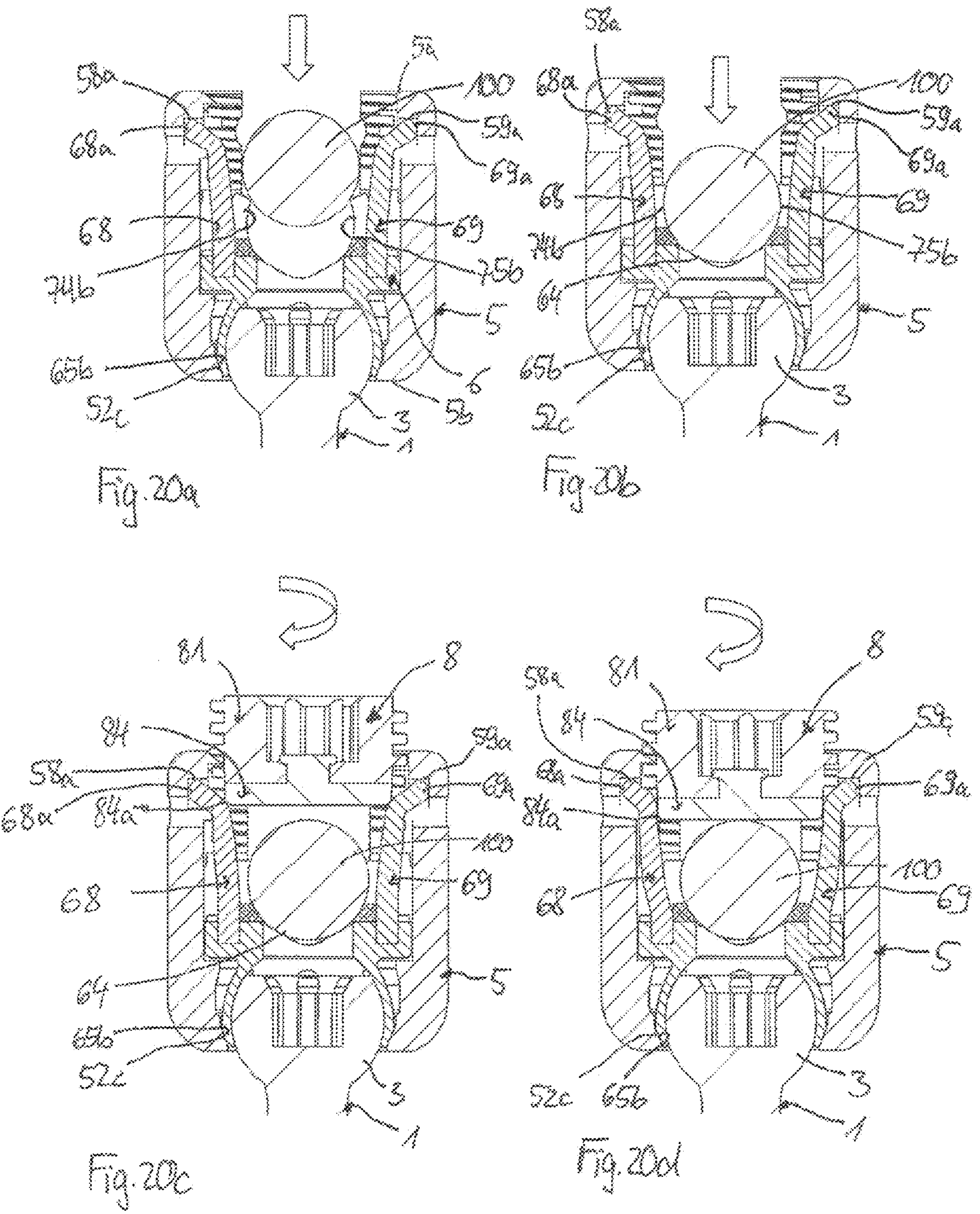
FIGS. 20*a* to 20*d* show cross-sectional views of inserting a rod into the polyaxial bone anchoring device and locking the rod and the head relative to the coupling device.

Next, the connection of the polyaxial bone anchoring device with a rod will be described with reference to FIGS. 20*a* to 20*d*. Usually, at least two bone anchoring elements 1 are inserted into bone parts or adjacent vertebrae, and the corresponding receiving parts 5 are aligned to receive the rod 100. Then, the rod 100 is inserted from the top end 5*a* of the receiving part 5 into the channel provided by the U-shaped recess 54 of the receiving part 5. Once the rod 100 passes the arms 74*a*, 74*b*, 75*a*, 75*b* of the rod retention member 7, the arms 74*a*, 74*b*, 75*a*, 75*b* are deflected outward and, due to their resiliency, snap back or just exert pressure to clamp the rod 100 by friction, as depicted in FIG. 20*b*. This allows an easier handling of the locking member 8 later, because wobbling of the rod 100 in the receiving part is prevented.

Next, as depicted in FIG. 20*c*, the locking member 8 is screwed in between the legs 55, 56 of the receiving part 5. When the locking member 8 is further screwed in, the lower rounded edge 84*a* of the washer 84 contacts the short portions 68*c*, 69*c* of the arms 68, 69 near the transition to the long portions 68*b*, 69*b*. Because the washer 84 is rotatably connected to the set screw 81, the washer 84 basically does not rotate when the set screw 81 is further advanced into the receiving part 5. This results in the forces exerted by the locking member 8 onto the arms 68, 69 being substantially axial, where radial forces and transverse forces are reduced. In the configuration shown in FIG. 20*c*, the rod 100 is still movable in a longitudinal direction along the rod axis because the locking member 8 is not yet in contact with the rod 100.

The locking member 8 exerts a force onto the arms 68, 69 that deforms the arms 68, 69, as can be seen in FIG. 20*d*. Because the free ends 68*a*, 69*a* of the arms 68, 69 are supported in the receiving part 5 and the pressure member 6 with the inserted head 3 is supported in the narrowing portion 52*c* of the receiving part 5, there is limited or no space for the arms 68, 69 to extend in the axial direction, so the long portions 68*b*, 69*b* of the arms 68, 69 are deflected radially outward, as depicted in FIG. 20*d*. The deformation of the arms 68, 69 results in a continuously increasing pressure onto the head 3. The arms 68, 69 are further deformed outward during tightening of the locking member 8 and extend into the space provided by the first bore 51. When the arms 68, 69 are in a second configuration, as shown in FIG. 20*d*, the head 3 is fully locked by the pressure exerted by the pressure member 6. The second configuration is maintained even if the locking member 8 is advanced further downward, such that the locking member 8 slides along the inner sides of the arms 68, 69, so that the advancement of the locking member 8 relative to the arms 68, 69 may require only little force while the pressure member 6 is in the second configuration.

A loosening of the locking member 8 causes the arms 68, 69 to return to the first configuration due to the high elasticity of the arms 68, 69. After loosening the locking member 8, the positions of the head 3 and the rod 100 relative to the receiving part 5 can be adjusted again.

Figures 17A, 17B:
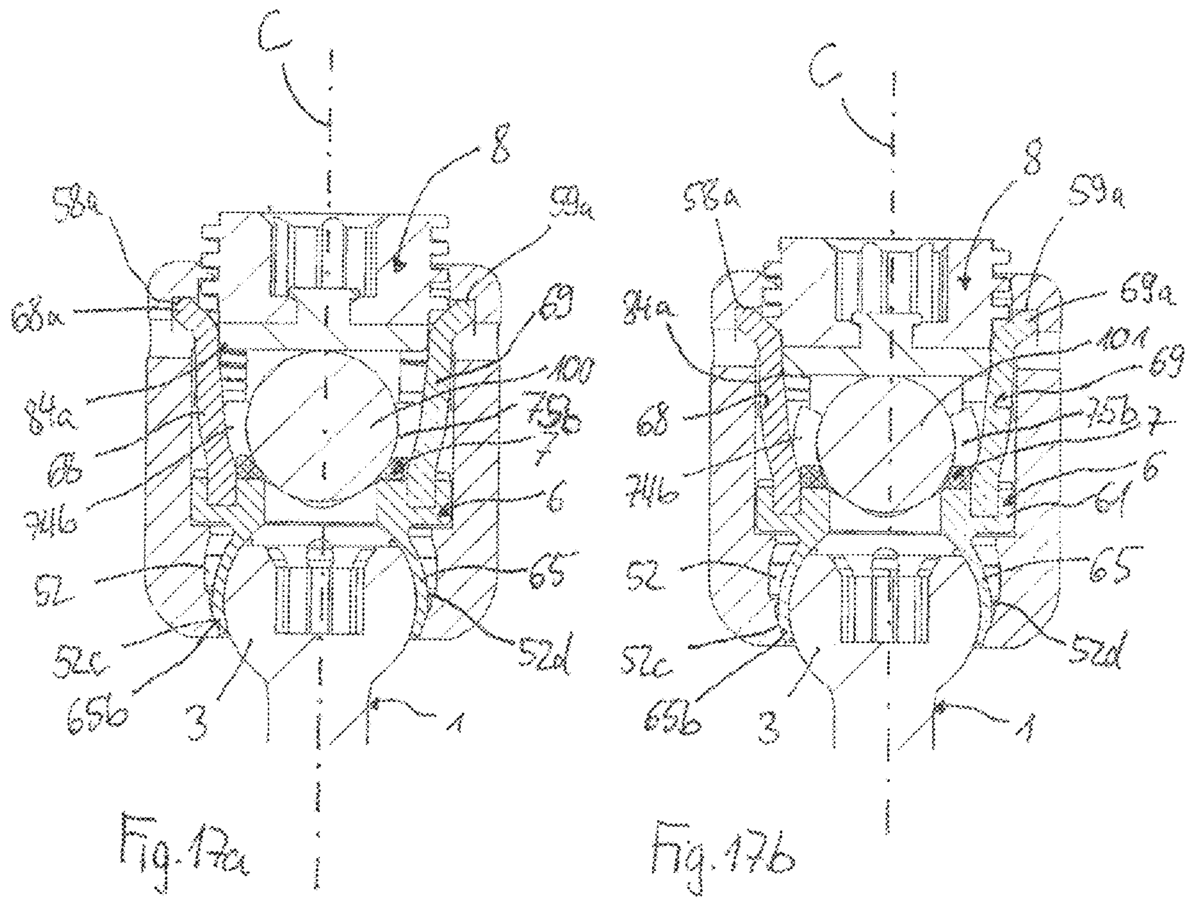
FIG. 17*a* shows a cross-sectional view of the polyaxial bone anchoring device of FIG. 2 with an inserted rod having a first diameter in an assembled and locked condition, the cross-section taken in a plane including a central axis of the device and extending perpendicular to a longitudinal direction of the inserted rod.
FIG. 17*b* shows a cross-sectional view of the polyaxial bone anchoring device of FIG. 2 with an inserted rod having a second diameter, smaller than the first diameter, in an assembled and locked condition, the cross-section taken in a plane including a central axis of the device and extending perpendicular to a longitudinal direction of the inserted rod.

Further, a system can include the polyaxial bone anchoring device and at least two rods 100, 101 having different diameters, where the bone anchoring device is configured to receive any of the rods (see, e.g., FIGS. 17*a*, 17*b*). FIG. 17*a* shows a polyaxial bone anchoring device according to an embodiment of the invention being used with a rod 100. If a rod of a different diameter than the rod 100 is used, for example, the rod 101 with a smaller diameter than the rod 100, the rod 101 can also be safely supported on the rod supporting surface 64 of the pressure member 6 and clamped by the arms 74*a*, 74*b*, 75*a*, 75*b* of the rod retention member 7, as depicted in FIG. 17*b*. Due to the smaller diameter of the rod 101, the arms 74*a*, 74*b*, 75*a*, 75*b* extend to a higher position on the rod 101 when viewed from the rod supporting surface 64, which can compensate for a reduced friction hold when compared to use with the rod 100 which has the larger diameter. The system allows the surgeon to select an appropriate rod depending on the desired application.

Further modifications of the above described embodiments are also conceivable. For example, the arms of the pressure member can have any of many different shapes as long as a deformation from a first configuration to a second configuration is possible. Even one single arm may be sufficient in some embodiments. In addition, the arms need not be continuous pieces. For example, it is possible to construct the arms from two substantially rigid levers that are connected via a hinge to form a toggle lever. In this case, the deformation may involve, for example, bringing the toggle lever from a first, angled configuration to a second, more substantially straight configuration. In some embodiments, the pressure member can be a monolithic piece that is made of a material exhibiting high elasticity.

In another embodiment, the locking of the head is maintained by the pressure exerted by the pressure member in the second configuration, even if the locking member is loosened. Hence, further adjustments of the rod position are possible while the head still remains in the locked angular position. In such an embodiment, the deformable portion can be adjusted back to the first configuration, for example, by applying an instrument through the through-holes 58*c*, 59*c* in the receiving part 5.

The rod retention member can further have any shape that allows holding of the rod. The arms of the rod retention member can be otherwise shaped, and/or there can be less or more than four arms. In some cases a single arm or clip may be sufficient. The rod retention member can also be formed as a monolithic piece with the pressure member. Also, in some embodiments, the rod retention member can be used in connection with bone anchoring devices that are of the top loading type, where the bone anchoring element is inserted from the top end.

In different embodiments, the pressure member can act via a direct contact onto the head, or may instead be operatively in contact with the head via, for example, an additional intermediate part.

Meanwhile, for the bone anchoring element, different kinds of bone anchoring elements can be used, such as screws, nails, cannulated anchors, hooks, etc. In some embodiments, the head and the shank may be constructed from two pieces that connect to one another. Although the head in the described embodiments is shown to have a spherical segment shape, such that the bone anchoring element is polyaxially pivotable with respect to the receiving part, in some embodiments, the head and/or the receiving part or the pressure member may instead be designed such that pivoting can only take place, for example, in one single plane. The polyaxial bone anchoring device may also be designed such that larger pivot angles between the bone anchoring element and the receiving part in particular directions is possible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A polyaxial bone anchoring device comprising:
- a bone anchoring element comprising a shank for anchoring to bone and a head;
- a receiving part having a first end, a second end below the first end, a longitudinal axis extending through the first and second ends, a channel at the first end for receiving a rod, an accommodation space for pivotably holding the head of the bone anchoring element, and an opening at the second end sized to facilitate insertion of the head therethrough to a seat in the accommodation space;
- a pressure member positionable in the receiving part and comprising an upwardly facing surface having at least a portion configured to extend into the channel to engage the rod and a downwardly facing surface having at least a portion configured to exert pressure on the head to lock the head relative to the receiving part; and
- a pair of expandable members, wherein when the pressure member is in the receiving part, each of the expandable members is configured to extend from the upwardly facing surface of the pressure member towards the first end of the receiving part to a free end surface that is configured to directly engage the receiving part, and wherein the expandable members are configured to be positioned on opposite sides of the channel for the rod, respectively, and are directly accessible from the first end;
- wherein when the head and the pressure member are in the receiving part, the expandable members are axially expandable in a direction of the longitudinal axis to urge the pressure member away from the first end of the receiving part to increase the pressure exerted on the head.

2. The polyaxial bone anchoring device of claim 1, wherein the expandable members are expandable axially to a configuration where the pressure member exerts a force on the head that is sufficient to lock the head relative to the receiving part.

3. The polyaxial bone anchoring device of claim 1, wherein the pressure member is configured to assume an insertion position where the head is insertable through the opening at the second end of the receiving part to the seat.

4. The polyaxial bone anchoring device of claim 1 wherein the pressure member is configured to assume a pre-locking position where the head is restricted from being removed from the receiving part.

5. The polyaxial bone anchoring device of claim 1, wherein the expandable members are elastically deformable.

6. The polyaxial bone anchoring device of claim 1, further comprising a locking member insertable into the channel and comprising an engagement surface that is engageable with the receiving part to lock the rod in the channel, wherein the expandable members are configured to protrude radially into a path of the locking member when the locking member is advanced into the channel.

7. The polyaxial bone anchoring device of claim 1, wherein the expandable members form arms that extend upwardly from the upwardly facing surface of the pressure member.

8. The polyaxial bone anchoring device of claim 1, wherein the expandable members are separable from and connectable to the pressure member.

9. The polyaxial bone anchoring device of claim 8, wherein each of the expandable members extends axially into the upwardly facing surface of the pressure member.

10. The polyaxial bone anchoring device of claim 1, wherein the pressure member is prevented from extending to an axial position that is higher than the free end surfaces of the expandable members.

11. The polyaxial bone anchoring device of claim 1, wherein at least part of each of the expandable members is movable radially relative to the longitudinal axis.

12. The polyaxial bone anchoring device of claim 11, wherein the at least part of each of the expand members is movable radially relative to the longitudinal axis while a radial position of the free end surface of the expandable member remains constant.

13. A polyaxial bone anchoring device comprising:
- a bone anchoring element comprising a shank for anchoring to bone and a head;
- a receiving part having a first end, a second end below the first end, a longitudinal axis extending through the first and second ends, a channel at the first end for receiving a rod, an engagement surface at the first end for engaging a locking member to lock the rod in the channel, first and second abutments positioned axially higher than a bottom of the engagement surface, and an accommodation space at the second end for pivotably holding the head of the bone anchoring element;

a pressure member positionable in the receiving part and comprising a downwardly facing surface having at least a portion configured to exert pressure on the head to lock the head relative to the receiving part; and at least one flexible member, wherein when the pressure member is in the receiving part the flexible member is configured to extend from the pressure member towards the first end of the receiving part to a free end surface that is configured to directly engage the receiving part;

wherein when the pressure member is in the receiving part, the free end surface of the flexible member is configured to engage the first abutment of the receiving part to hold the pressure member at an insertion position where the head is insertable from the second end of the receiving part into the accommodation space; and wherein when the head and the pressure member are in the receiving part, the free end surface of the flexible member is movable axially downwardly to engage the second abutment positioned axially lower than the first abutment to hold the pressure member at a pre-locking position to restrict removal of the head from the receiving part.

14. The polyaxial bone anchoring device of claim 13, wherein the engagement surface at the first end of the receiving part comprises a thread, and wherein the first and second abutments are positioned higher axially than the bottom of the thread.

15. The polyaxial bone anchoring device of claim 13, wherein the first and second abutments is each configured to restrict upward movement of the pressure member relative to the receiving part.

16. The polyaxial bone anchoring device of claim 13, wherein the flexible member is formed as part of the pressure member and forms an arm that extends upwardly from other portions of the pressure member in the receiving part.

17. A polyaxial bone anchoring device comprising:

a bone anchoring element comprising a shank for anchoring to bone and a head;

a rod;

a receiving part having a first end, a second end below the first end, a longitudinal axis extending through the first and second ends, a channel at the first end for receiving the rod, an accommodation space for pivotably holding the head of the bone anchoring element, and an opening at the second end sized to facilitate insertion of the head therethrough into the accommodation space; and a monolithic pressure member positionable in the receiving part and comprising a downwardly facing surface having at least a portion configured to exert pressure on the head to lock the head relative to the receiving part and a rod retention surface;

wherein when the pressure member is held in the receiving part at an insertion position, the head is insertable through the opening at the second end into the accommodation space, while the rod is insertable into the channel and configured to be clamped relative to at least the pressure member by the rod retention surface.

18. The polyaxial bone anchoring device of claim 17, wherein when the head is held in the accommodation space, the rod is insertable into the channel and configured to be clamped by the rod retention surface while a pressure exerted by the pressure member on the head remains substantially constant.

* * * * *